United States Patent [19]

Warwel et al.

[11] Patent Number: 5,321,158
[45] Date of Patent: Jun. 14, 1994

[54] PRODUCTION OF CARBOXYLIC ACIDS

[75] Inventors: Siegfried Warwel, Hans-Böckler-Allee; Mark R. G. Klaas, Katthagen, both of Fed. Rep. of Germany

[73] Assignee: Solvay Interox GmbH, Fed. Rep. of Germany

[21] Appl. No.: 96,418

[22] Filed: Jul. 26, 1993

[51] Int. Cl.$^5$ .................. C07C 51/16; C07C 57/02
[52] U.S. Cl. .................. 562/544; 562/546; 562/590; 562/595
[58] Field of Search .............. 562/544, 546, 590, 595

[56] References Cited

U.S. PATENT DOCUMENTS 3,646,130  2/1972  Parshall .................. 562/543

OTHER PUBLICATIONS

Warwel, et al., "Selective Oxidations in Petrochemistry", DGMK-Conference, Sep. 16-18, 1992 in Goslar/Germany.
Haines, A. H., "Formation of Carboxylic Acids", Methods for the Oxidation of Organic Compounds, pp. 146-152.
Zaidman, et al., "Double Bond Oxidation of Unsaturated Fatty Acids", JAOCS, vol. 65, No. 4 (Apr. 1988), pp. 611-615.

Primary Examiner—José G. Dees
Assistant Examiner—Joseph M. Conrad, III
Attorney, Agent, or Firm—Larson and Taylor

[57] ABSTRACT

An improved process for the production of carboxylic acids and dicarboxylic acids by the catalytic oxidation of olefins and vicinal diols by hydrogen peroxide is provided. The process employs a rhenium (VII) catalyst, and a solvent comprising a mixture of a carboxylic acid or anhydride having 2 or more carbon atoms and a high boiling cyclic or acyclic ether. Particularly suitable carboxylic acids or anhydrides include acetic acid, propionic acid and acetic anhydride. Particularly suitable high-boiling ethers include 1,4-dioxane and diglyme.

21 Claims, No Drawings

PRODUCTION OF CARBOXYLIC ACIDS

The invention relates to a process for the production of carboxylic acids or dicarboxylic acids by the catalytic oxidation of C=C bonds in olefins and functionalised olefins by means of $H_2O_2$ used as oxidising agent and Re(VII) compounds used as catalysts.

Carboxylic acids and aliphatic dicarboxylic acids are compounds of industrial importance. They are used in the field of detergents and cleaning agents as well as cosmetics. $\alpha,\Omega$-dicarboxylic acids are important monomers in synthetic resin manufacture (polyesters, polyamides). Whereas long-chain, even-numbered carboxylic acids occur in the form of triglycerides in natural oils and fats and can be obtained from them, carboxylic acids with an uneven number of carbon atoms must be produced by a synthetic route.

One method for the production of fairly long-chain carboxylic acids with an uneven number of carbon atoms takes the form of nitrile synthesis. This process involves several stages, is expensive and involves the hazards associated with working with HCN.

An alternative method is to employ the hydrocarboxylation of even numbered $\alpha$-olefins. However, this process gives mixtures of linear carboxylic acids with an uneven number of C atoms and also containing undesirable branched isomers (see A. Weiss, Fat Science Technology 92, 392 (1990)).

Dicarboxylic acids used as starting products for the manufacture of polyesters and polyamides are produced on an industrial scale by the oxidation of cyclo-alkanes via the cycloalkanols/alkanones stage. However, this route gives only dicarboxylic acids with a chain length corresponding to the cycloalkanes readily available, most commonly C6, C8 and C12.

The standard method for the oxidative cleavage of C=C bonds to carboxylic acids is ozonolysis with subsequent oxidative processing. It is, for example, used on an industrial scale in the oxidative cleavage of oleic acid to nonanoic and nonanedioic acid. However, this method has not found widespread industrial application because the use of ozone involves a relatively high cost and also there are safety problems during the handling of ozone (See. B. Zaidmann et al., J. Am. Oil Chem. Soc 65. 61 (1988)).

The cleavage of C=C bonds by means of active oxygen compounds and transition metal catalysis is also known. Possibly the most well known process in this connection makes use of the Ru(VII)/peracetic acid system (see for example A. H. Haines, Methods for the Oxidation of Organic Compounds, S. 146-52, Academic Press, London 1985), which converts olefins via cyclic perruthenate esters to carboxylic acids. However this process has the disadvantage that highly toxic $RuO_4$ is formed as an intermediate.

American Patent U.S. Pat. No. 3,646,130 (G. W. Parschall, Du Pont) of Feb. 29, 1972 describes the oxidative cleavage of cyclododecene with $H_2O_2$ to carboxylic acids (if necessary with an addition of carboxylic anhydride) as solvent and $Re_2O_7$ as catalyst. With a catalyst concentration of 2 mole %, a maximum yield of 1,12-dodecanedioic acid of only 30% is obtained.

Organometallic rhenium compounds are described in DE-OS 3902357 dated Jan. 27, 1989 for the catalysis of the epoxidation of olefinic double bonds. The teaching of W. A. Herrmann, R. W. Fischer and D. W. Marz, Angew. Chem. 103, 1706-9 (1991) is that these compounds are unsuitable for oxidative cleavage.

It was therefore one object of the present invention to develop a process for the production of carboxylic acids and/or dicarboxylic acids by the oxidative cleavage of C=C bonds, which does not have or ameliorates the disadvantages of the state of the art.

In particular, it is a further object of at least some embodiments to develop a process which provides carboxylic acids and/or dicarboxylic acids in high yield by using lower toxicity, reusable catalysts.

According to the present invention there is provided an improved process for the production of carboxylic acids and dicarboxylic acids by the oxidative cleavage of olefinically unsaturated compounds or vicinal diols in the presence of an organic solvent with a Re(VII) compound as catalyst and $H_2O_2$ used as oxidising agent in a solvent mixture comprising:

i. a carboxylic acid or carboxylic anhydride having 2 or more carbon atoms, and.

ii. a high-boiling cyclic or acyclic ether having one or more ether groups.

The carboxylic acid or anhydride having 2 or more carbon atoms of the process according to the present invention can be any such acid or anhydride which is liquid at the temperature at which the process is carried out or forms a solution under the operating conditions. Preferably, the carboxylic acid or anhydride has no more than 6 carbon atoms. It will be recognised that such compounds can be either linear or branched, but in most embodiments, it is convenient to employ linear examples. Particularly suitable examples include acetic acid, propionic acid and acetic anhydride.

The high boiling ether of the process according to the present invention can be any such ether which is liquid at the temperature at which the process is carried out or forms a solution under the operating conditions. The ether can be cyclic or acyclic, and can be linear or branched. The boiling point of such high boiling ethers is typically greater than about 75° C. Suitable examples include ethylene glycol dimethyl ether, diethylene glycol dimethyl ether, ethylene glycol diethyl ether and 1,4-dioxane.

In the process according to the present invention, the solvents can be present in a wide range of volume ratios, and the ratio can be selected in order to achieve, for example, a particular solubility or a particular boiling point. Typically, the volume ratio of acid or anhydride to ether is selected within the range of from 10:1 to 1:25, and preferably from 2:1 to 1:2.

Examples of the Re(VII) compounds used as catalysts in the process according to the present invention include $Re_2O_7$ and the perrhenates with the general formula $M(ReO_4)$ and $M'(ReO_4)_2$, M being an alkali metal or ammonium, such as $NH_4ReO_4$, and M' an alkaline earth metal. The rhenium (VII) compounds may be generated in situ in the reaction mixture. In such embodiments, they are introduced in the form of compounds of a low oxidation state, including metallic rhenium or rhenium(O) carbonyl complexes such as $Re_2(CO)_{10}$, since they are oxidised by the $H_2O_2$ present in the reaction mixture to form catalytically active rhenium(VII) compounds. It is also possible to employ organorhenium compounds, such as methyl trioxorhenium.

For a process according to the invention, the catalyst is preferably used in concentrations of 0.1 to 5 mole % based on an oxidisable C=C bond of the olefinically unsaturated starting compound or oxidisable vicinal diol group. The use of the catalyst in concentrations of 0.25 to 1 mole %, based on an oxidisable C=C bond of the olefinically unsaturated starting compound or oxidisable vicinal diol group, is particularly preferred.

The catalysts used in the process according to the present invention have the additional advantage that they remain in the reaction medium after the reaction products have been separated off, e.g. by filtration and can be reused in this form as catalyst solution without any or undue decrease in catalytic activity or any regeneration or activation of the catalyst having to take place. In this way, repeated re-use of the catalyst is possible.

The compounds that can be oxidised by the process according to the present invention, hereinafter referred to as substrates, include olefinically unsaturated compounds such as cyclic or acyclic compounds with one or several C=C bonds, i.e. monoolefins, diolefins or polyenes. In the case of acyclic olefins, the C=C bonds can be either terminal or embedded within the molecule. These compounds may be substituted by one or more functional groups such as e.g. an aryl group or, to particular advantage, a carboxylic acid or carboxylic acid ester group. Examples of suitable open-chain, unsubstituted olefins are e.g. 1-octene or 7-tetradecene. Examples of substituted olefins are e.g. 10-undecenoic acid or oleic acid methyl ester.

Other substrates include vicinal diols. It will be recognised that such compounds are often formed as intermediates in the oxidation of olefins which then undergo further oxidation, but in certain embodiments, it is possible to employ such a vicinal diol as the starting material. This is particularly so where the vicinal diol is symmetrical, has an even number of carbon atoms and has the diol grouping located on the central carbon atoms. The process according to the present invention allows oxidation of such substrates to produce substantially a single acid product.

The hydrogen peroxide used in the process according to the present invention is typically employed as an aqueous solution having a concentration of 30–90% w/w, preferably at least 60%, and especially 80 to 85% w/w. The molar ratio of $H_2O_2$ to an oxidisable double bond of the olefinically unsaturated compound or vicial diol group is often 1:1 to 8:1, and is preferably 2:1 to 6:1.

The oxidation temperatures employed are typically between ambient temperature and 100° C., and are preferably at or within 5° C. of the boiling point of the solvent mixture used.

In one convenient method of carrying out the reaction, the substrate, the solvent and the catalyst are placed into a vessel. Subsequently, the mixture is brought to reaction temperature followed by the progressive addition of $H_2O_2$ typically introduced over a period of from 20 to 120 minutes, either continuously or in small discrete additions. On completion of the reaction, the reaction mixture is cooled and a mild reducing agent (e.g. $Na_2SO_3$ in aqueous solution) is added. Preferably, the reaction mixture is cooled to a temperature lower than ambient, and most preferably to about 0° C. The reaction products can be isolated from the resulting mixture e.g. by extraction with organic solvents or, if they are insoluble, by filtration.

In certain embodiments, slightly higher yields of the resulting carboxylic acids can be obtained by combining the $H_2O_2$ with the solvent and the catalyst and then adding the substrate progressively at the desired reaction temperature. However, such a procedure is not recommended in that it maximises the concentration of hydrogen peroxide in an organic system thereby increasing the risk that the mixture as a whole or locally is detonable.

On completion of the addition of hydrogen peroxide, or substrate as the case may be, the reaction is usually maintained at the reaction temperature for a further period of time during which stirring is maintained. It will be recognised that this further reaction period can vary over a wide range of times, and may depend, for example, on the reactivity of the substrate and/or the other prevailing reaction conditions. The further reaction time can extend to 24 hours and beyond, but in many embodiments will be between 5 and 20 hours. Where a particularly reactive substrate is employed, the further reaction time may even be less than 5 hours, such as from 1 to 4 hours.

The fact that Re(VII) compounds are highly suitable, in these solvents, as catalysts for the oxidative cleavage of olefinic double bonds is highly surprising in view of the state of the art. The teaching of W. A. Herrmann, R. W. Fischer and D. W. Marz, Angew. Chem. 103, 1706-9 (1991) is that the organometallic rhenium compounds described in DE-OS 3902357 dated Jan. 27, 1989, which catalyse the epoxidation of olefinic double bonds are unsuitable for oxidative cleavage. However, it has been found that these compounds, too, catalyse the oxidative cleavage in the process according to the present invention.

The invention is illustrated in further detail by way of the following examples.

EXAMPLE 1

Oxidative cleavage of 1-octene 0.05 mole 1-octene (5.6 g) were dissolved in a mixture of 10 ml acetic anhydride and 10 ml 1,4-dioxane, and 0.5 mmole $Re_2O_7$ (0.24 g) was added. Subsequently, the temperature was increased to 90° C. $H_2O_2$ to give a mole ratio of $H_2O_2$:substrate of 5:1 (10 grams, 85% w/w) was added dropwise slowly with stirring. After 16 hours at 90° C., the reaction mixture was worked up by cooling to 0° C. and approximately 30 ml saturated sodium sulphite solution was added. The solution was acidified with 10% HCl, extracted repeatedly with ether and the combined organic extracts were concentrated in a rotary evaporator.

The remaining product mixture was subjected to gas chromatographic analysis. Apart from heptanoic acid, the main product, it contained 1,2-octane diol and smaller quantities (2–5% based on the olefin used) of 1-acetoxy-2-octanol, 2-acetoxy-1-octanol, 1-heptanoxy-2-octanol and 2-heptanoxy-1-octanol. By adding a GC standard (enanthic acid ethyl ester), the amounts of the two main products formed were determined quantitatively, taking the correction factors determined previously by means of pure substances into consideration.

Yield of heptanoic acid: 53% of the theoretical based on olefin.

Yield of 1,2 octane diol: 12% of the theoretical based on olefin.

EXAMPLE 2

Oxidation of 7-tetradecene 0.03 mole 7-tetradecene (5.9 grams) were dissolved in a mixture of 10 ml acetic anhydride and 10 ml 1,4-dioxane, and 0.3 mmole $Re_2O_7$ (0.14 grams) were added.

Subsequently, the temperature was increased to 90° C. and $H_2O_2$ to give a mole ratio of $H_2O_2$:substrate of 5:1 (6.0 grams, 85% w/w) was slowly added dropwise with stirring. Subsequently, stirring was continued for 16 hours at 90° C. Work up and analysis were as for Example 1.

Yield of heptanoic acid: 54% of the theoretical based on olefin.

EXAMPLE 3

Oxidation of 7-tetradecene employing Propionic acid as co-solvent

The procedure of Example 2 was followed, except that a mixture of 10 ml propionic acid and 10 ml 1,4-dioxane was employed as solvent.

Yield of heptanoic acid: 47% of the theoretical based on olefin.

EXAMPLE 4

Oxidation of 7-tetradecene with Diglyme as co-solvent

The procedure of Example 2 was followed, except that a mixture of 10 ml acetic anhydride and 10 ml diethylene glycol dimethyl ether (diglyme) was employed as solvent.

Yield of heptanoic acid: 51% of the theoretical based on olefin.

EXAMPLE 5

Oxidation of 7-tetradecene employing $Re_2(CO)_{10}$ as catalyst

The procedure of Example 2 was followed, except that 0.3 mmole $Re_2(CO)_{10}$ (196 grams) was employed as catalyst.

Yield of heptanoic acid: 54% of the theoretical based on olefin.

EXAMPLE 6

Oxidation of 7-tetradecene employing metallic Re as catalyst

The procedure of Example 2 was followed, except that 0.3 mmole metallic rhenium (56 mg) was employed as catalyst, the Re (VII) catalytic species being generated in situ.

Yield of heptanoic acid: 50% of the theoretical based on olefin.

EXAMPLE 7

Oxidation of 7-tetradecene employing $NH_4ReO_4$ as Catalyst

The procedure of Example 2 was followed, except that 0.3 mmole $NH_4ReO_4$ (80 mg) was employed as catalyst.

Yield of heptanoic acid: 55% of the theoretical based on olefin.

EXAMPLE 8

Oxidation of 7-tetradecene employing a different order of reagent addition 0.3 mmole $Re_2O_7$ (0.14 g) was added to a mixture of 10 ml acetic anhydride and 10 ml 1,4-dioxane in the dissolved state. Subsequently, 0.15 mole $H_2O_2$ (6.0 grams, 85% w/w) was added slowly dropwise. Once the exothermal dissolution process has died down, the temperature was increased to 90° C. and 0.03 mole 7-tetradecene (5.9 grams) were added dropwise over approximately 30 minutes. Stirring was then carried out for 16 hours at 90° C. Work up and analysis were as for Example 1.

Yield of heptanoic acid: 62% of the theoretical based on olefin.

EXAMPLE 9

Oxidation of 7-tetradecene employing methyl trioxorhenium as catalyst

The procedure of Example 2 was followed, except that 0.3 mmole methyl trioxorhenium (75 mg) was employed as catalyst.

Yield of heptanoic acid: 47% of the theoretical based on olefin.

EXAMPLE 10

Oxidation of 9-octadecene

The procedure of Example 2 was followed, except that 0.03 mole 9-octadecene (6.1 grams) was employed as substrate. Decanoic acid ethyl ester was used as gas chromatographic internal standard.

Yield of nonanoic acid: 55% of the theoretical based on olefin.

EXAMPLE 11

Oxidation of oleic acid methyl ester

The procedure of Example 2 was followed, except that 0.03 mole oleic acid methyl ester (84% w/w, 10.6 grams) was employed as substrate. Phthalic acid diethyl ester was used as gas chromatographic internal standard.

Yield of nonanoic acid: 52% of the theoretical based on olefin.

Yield of nonane dioic acid monomethyl ester: 55% of the theoretical based on olefin

EXAMPLE 12

Oxidation of 7,8-tetradecanediol

The procedure of Example 2 was followed, except that 0.03 mole 7.8-tetradecanediol (7.1 g) was employed as substrate and $H_2O_2$ to give a mole ratio of $H_2O_2$:substrate of 3:1 (3.6 g, 85% w/w) was added.

Yield of heptanoic acid: 62% of the theoretical based on the diol used.

EXAMPLE 13

Oxidation of 10 undecenoic acid methyl ester

The procedure of Example 2 was followed, except that 0.03 mole 10-undecenoic acid methyl ester (6.0 g) was employed as substrate. For work up, the mixture was cooled to 0° C. and aqueous sodium sulphite solution was added until the peroxides were destroyed. Subsequently, the mixture was acidified with 10% HCl. The solid precipitated out, a white powder, was filtered off, drying takes place until a constant weight was obtained followed by gas chromatographic analysis.

Yield of decane dioic acid monomethyl ester: 68% of the theoretical based on the ester used. (Approximately 12% 10,11di-hydroxyundecanoic acid methyl ester was obtained as a by-product).

In the same way, 9-decenoic acid methyl ester can be reacted to form nonane dioic acid monomethyl ester (yield 61% of the theoretical based on the ester used) and 13-tetradecenoic acid methyl ester can be reacted to tridecanoic acid monomethyl ester (yield 84%).

EXAMPLE 14

Oxidation of 10-undecenoic acid

The procedure of Example 2 was followed, except that 0.03 mole 10-undecenoic acid (5.7 g) was employed as substrate. Decanoic acid ethyl ester was used as gas chromatographic internal standard.

Yield of decane dioic acid: 67% of the theoretical based on the undecenoic acid used.

EXAMPLE 15

Oxidation of 10-undecenoic acid methyl ester employing reduced substrate: catalyst ratio 0.03 mole 10-undecenoic acid methyl ester (6.0 g) were dissolved in a mixture of 10 ml acetic anhydride and 10 ml 1,4-dioxane and 0.075 mmole $Re_2O_7$ (0.36 mg) was added. Subsequently, the temperature was increased to 90° C. and 0.15 mole $H_2O_2$ (6.0 grams, 85% w/w) was added slowly dropwise with stirring. Stirring was then continued for 16 hours at 90° C. Work up and analysis were as for Example 13.

Yield of decanedioic acid monomethyl ester: 66% of the theoretical based on the ester used.

EXAMPLE 16

Oxidation of 7-tetradecene with 1:19 volume ratio of anhydride to ether

The procedure of Example 2 was followed, except that a mixture of 1 ml acetic anhydride and 19 ml 1,4-dioxane was employed as solvent.

Yield of heptanoic acid: 46% of the theoretical based on olefin.

COMPARISONS 17 AND 18 ARE COMPARATIVE TRIALS ACCORDING TO U.S. Pat. No. 3,646,130

Comparison 17

Oxidation of 7-tetradecene 0.03 mole 7-tetradecene (5.9 g) were dissolved in 30 ml acetic acid and 0.6 mmole $Re_2O_7$ (0.29 g) were added dropwise. 0.0.15 mole $H_2O_2$ (15.0 grams, 30% w/w) were slowly added dropwise with stirring. Subsequently, stirring took place for 1 hour at room temperature and for 5 hours at 100° C. Work up and analysis were as for Example 1.

Yield of heptanoic acid: 30% of the theoretical based on olefin.

Comparison 18

Oxidation of 10-undecenoic acid methyl ester 0.03 mole 10-undecenoic acid methyl ester (6.0 g) were dissolved in 30 ml acetic acid and 0.6 mmole $Re_2O_7$ (0.29 g) were added dropwise. 0.15 mole $H_2O_2$ (15.0 grams, 30% w/w) were slowly added dropwise with stirring. Subsequently, stirring took place for 1 hour at room temperature and for 5 hours at 100° C. Work up and analysis were as for Example 13.

Yield of decane dioic acid monomethyl ester: 26% of the theoretical based on olefin.

Comparison 19

Oxidation of 7-tetradecene with Hexane as co-solvent 0.03 mole 7-tetradecene (5.9 g) were dissolved in a mixture of 10 ml acetic anhydride and 10 ml n-hexane and 0.3 mmole $Re_2O_7$ (0.14 g) was added. Subsequently, the temperature was increased to 90° C. and 0.15 mole $H_2O_2$ (6.0 grams, 85% w/w) was added slowly dropwise with stirring. Stirring was then continued for 16 hours at 70° C. Work up and analysis were as for Example 1.

Yield of heptanoic acid: 35% of the theoretical based on olefin.

The results of Examples 1 to 16 show that very good yields were achieved using the process according to the present invention. The results of Comparisons 17 and 18 show that only poor yields were obtained by the process according to U.S. Pat. No. 3,646,130. The result of Comparison 19 shows that replacement of the high-boiling ether with a solvent such as hexane also gave poor results.

We claim:

1. In a process for the production of carboxylic acids and dicarboxylic acids by the oxidative cleavage of olefinically unsaturated compounds or vicinal diols in the presence of an organic solvent with a Re(VII) compound used as catalyst and $H_2O_2$ used as oxidising agent, the improvement comprising a solvent mixture comprising:
   i. a carboxylic acid or carboxylic anhydride having 2 or more carbon atoms, and.
   ii. a high-boiling cyclic or acyclic ether having one or more ether groups.

2. A process according to claim 1, wherein the carboxylic acid or anhydride has no more than 6 carbon atoms.

3. A process according to claim 2, wherein the carboxylic acid or anhydride is acetic acid or acetic anhydride.

4. A process according to claim 1, wherein the high boiling ether comprises 2 to 4 ether groups.

5. A process according to claim 4, wherein the high boiling ether is 1,4-dioxane.

6. A process according to claim 4, wherein the high boiling ether is selected from ethylene glycol dimethyl ether or diethylene glycol dimethyl ether.

7. A process according to claim 1, wherein the volume ratio of carboxylic acid or anhydride to ether is from 10:1 to 1:25.

8. A process according to claim 7, wherein the volume ratio of carboxylic acid or anhydride to ether is from 2:1 to 1:2.

9. A process according to claim 1, wherein the rhenium (VII) catalyst is selected from the group comprising $Re_2O_7$, $NH_4ReO_4$ and alkyltrioxorhenium.

10. A process according to claim 1, wherein the rhenium (VII) catalyst is produced in situ from rhenium in a lower oxidation state.

11. A process according to claim 10, wherein the rhenium (VII) catalyst is produced from metallic rhenium or $Re_2(CO)_{10}$.

12. A process according to claim 1, wherein the catalyst is present in an amount of 0.1 to 5 mole % based on the oxidisable C=C bond of the olefinically unsaturated starting compound or oxidisable vicinal diol group.

13. A process according to claim 12, wherein the catalyst is present in an amount of 0.25 to 1.2 mole % based on the oxidisable C=C bond of the olefinically unsaturated starting compound or oxidisable vicinal diol group.

14. A process according to claim 1, wherein the olefinically unsaturated compounds or vicinal diols are substituted by one or more functional groups selected from the group comprising carboxylic acid, carboxylic ester, and aryl groups.

15. A process according to claim 1, wherein the molar ratio of $H_2O_2$ to oxidisable double bond of the olefinically unsaturated compound or vicinal diol group is from 1:1 to 8:1.

16. A process according to claim 15, wherein the molar ratio of $H_2O_2$ to oxidisable double bond of the olefinically unsaturated compound or vicinal diol group is from 2:1 to 6:1.

17. A process according to claim 1, wherein the oxidation is carried out at a temperature of from ambient to 100° C.

18. A process according to claim 17, wherein the oxidation is carried out at or within 5° C. of the boiling point of the solvent mixture employed.

19. A process according to claim 1 wherein the products are separated from the reaction mixture and the residual liquor is recycled as catalyst solution.

20. A process according to claim 19, wherein the products are separated by filtration.

21. A process according to claim 1 or claim 8, wherein $Re_2O_7$ or $NH_4ReO_4$ is used as catalyst, and $H_2O_2$ used as oxidising agent at a molar ratio of $H_2O_2$ to oxidisable double bond of the olefinically unsaturated compound or vicinal diol group of from 2:1 to 6:1 in a solvent mixture comprising:
  i. acetic anhydride, and.
  ii. 1,4-dioxane.

* * * * *